United States Patent [19]

LeFevre et al.

[11] 4,038,981
[45] Aug. 2, 1977

[54] ELECTRONICALLY CONTROLLED INTRAVENOUS INFUSION SET

[75] Inventors: Robert J. LeFevre, Bethlehem; Robert E. Thomas, Wind Gap, both of Pa.

[73] Assignee: Burron Medical Products, Inc., Bethlehem, Pa.

[21] Appl. No.: 637,206

[22] Filed: Dec. 3, 1975

Related U.S. Application Data

[63] Continuation-in-part of Ser. No. 492,280, July 26, 1974, abandoned.

[51] Int. Cl.² .............................................. A61M 5/16
[52] U.S. Cl. ........................ 128/214 E; 128/DIG. 13; 137/487.5; 222/59.76
[58] Field of Search ........... 128/214 R, 214 C, 214 E, 128/214 F, 214.2, DIG. 12, DIG. 13; 251/123–125, 139, 141; 137/486, 487.5; 222/52, 59, 76, 420, 422

[56] References Cited

U.S. PATENT DOCUMENTS

| 2,096,808 | 10/1937 | Jenkins et al. | 251/141 X |
| 2,254,833 | 9/1941 | Ashkenaz | 128/213 |
| 3,163,176 | 12/1964 | Darling | 137/487.5 |
| 3,252,623 | 5/1966 | Corbin et al. | 128/214 E |
| 3,609,379 | 9/1971 | Hildebrandt | 222/52 X |
| 3,890,968 | 6/1975 | Pierce et al. | 128/214 E |

*Primary Examiner*—Dalton L. Truluck
*Attorney, Agent, or Firm*—Shoemaker and Mattare, Ltd.

[57] ABSTRACT

An electronically controlled, gravity-feed, intravenous infusion set in which a length of intravenous tubing is connected with a drip chamber to convey a fluid to be administered intravenously, the improvement comprising a normally closed internal valve in said set operable to prevent flow of fluid through the set and operated to open position to enable passage of a drop of fluid through the set, and an electrically controlled actuator operatively associated with the valve to operate the valve to its open position at a predetermined frequency of operation and to hold the valve open until a drop forms and falls to thus determine the drip rate of fluid through the set, said internal valve thus enabling control of flow of fluid through the set without necessitating crimping or other deformation of the set and thereby resulting in dependable and accurate control of the flow rate of the fluid to be administered intravenously.

14 Claims, 11 Drawing Figures

ELECTRONICALLY CONTROLLED INTRAVENOUS INFUSION SET

BACKGROUND AND SUMMARY OF THE INVENTION

This application is a continuation-in-part of application Ser. No. 492,280, filed July 26, 1974, now abandoned.

This invention relates to a parenteral administration set, and more particularly, to an intravenous infusion set for administering fluid to a patient and the like. Still more particularly, the invention relates to a disposable parenteral or intravenous infusion set which has an internal valve that is electronically controlled to accurately regulate the rate at which the fluid is fed intravenously to a patient.

In the prior art, various means have been used to control the rate of flow through IV sets for thus regulating the rate of intravenous administration of fluid to a patient. For example, manual flow control means have been provided in the form of clamps or the like, which are positioned on a length of IV tubing and are adjusted to pinch the tubing to enable more or less flow through the tubing and thus into the veins of a patient. Such devices are subject to irregular operation, however, due to changes in fluid pressure or due to human error in setting the clamps and the like. Electronically controlled devices have also been utilized, wherein an external, electromechanically operated valve is associated with the IV tubing to pinch the tubing and thus control the rate of flow therethrough dependent upon a signal from a timer which is preset to give a predetermined number of signals per unit of time. In such electronically controlled or operated devices, the circuits are relatively complicated and expensive, and the valve means utilized pinch or crimp or otherwise deform the tubing to control flow therethrough, thus substantially increasing the expense of the units and reducing the reliability thereof. For example, pinching of the IV tubing results in cold flow of the tubing with a consequent change in the flow rate therethrough. Still other prior art devices use electrically controlled valves which flutter, or operate at some multiple of the desired drip rate, or internal drop sensing means are used.

In accordance with the present invention, a solid state circuit is utilized to control an electromagnetically operated valve in the IV set to control the rate of flow therethrough. The set is of the gravity feed type and thus will not continue to feed fluid in the event the needle goes through a vein and into the surrounding tissue. The valve itself is an internal valve operable between open and closed positions without requiring deformation of the tubing or other parts of the set, and in one form of the invention comprises a reciprocating ball member which is normally maintained seated under the action of gravity and fluid pressure above the ball to thus prevent flow through the set and electromagnet means are disposed adjacent the ball to lift the ball from its seat whenever a signal is sent to the electromagnet means by a timer or clock mechanism. The timer generates a plurality of pulses per unit of time at a constant repetition rate, as determined by the setting on the clock or timer, and directly corresponding to the desired number of drops of IV fluid per unit of time. Moreover, permanent magnet means are preferably provided on the set to hold the valve open in the event of a power failure or the like, or to effect flushing of the set, or to transport the patient from one location to another, and a conventional clamp means may be used to regulate the flow in such event. External drop detecting means are also used, thus eliminating completely any penetration or deformation of the set.

The solid state circuit is exceptionally simple and reliable and is, therefore, substantially more economical than prior art devices and utilizes both integrated circuits and discrete components. All logic functions are accomplished via integrated circuits, and discrete components are used to limit and amplify current, establish time periods of the integrated circuits and form bias networks. The integrated circuits used are conventional N 7473 J-K bistable flip-flops, a conventional monostable flip-flop identified as Motorola Part No. C 3803, and conventional 555 integrated circuit chips. The circuit includes a variable clock or timer, a drop detector, a pulse shaper, a drop pulse extender, a drop indicator, a latch, a no-drop detector, a no-drop alarm and a no-drop indicator. As determined by the frequency adjustment of the clock, when a predetermined interval of time has elapsed, the clock will undergo a negative transition and send a negative pulse to the latch. This causes the latch to send a pulse or to generate a forward bias on a transistor switch, which energizes the electromagnet and thus opens the valve to enable a drop to form in the drip chamber. When the drop falls, it is sensed by the drop detector, which is entirely external of the flow path and which includes light sensitive means optically coupled across the drip chamber so that a falling drop interferes with the optical coupling, and which sends a signal to the pulse shaper, where the signal is amplified and squared up and then conducted to the drop pulse extender, which extends the width of the pulse to thus result in energization of the drop indicator for a period of time sufficient to be observed. The pulse shaper also sends a pulse to the latch or switch means to reset the latch and remove the bias from the transistor switch to thus de-energize the valve and enable the valve to close.

The output of the variable clock is also connected with the no-drop detector to trigger the no-drop detector, and an output of the drop pulse extender is also connected with the no-drop detector to reset the no-drop detector. This output of the drop pulse extender undergoes a change of state substantially simultaneously with the changes of state of the pulse shaper. Thus, if no drop is detected, the no-drop detector will not be reset and the output of the no-drop detector, which is fed to the J input of the latch, will cause the latch to respond to the next clock pulse by driving its Q output low, and will thereafter maintain the latch at a "zero" as long as no drops are detected. The no-drop detector is itself locked up by the drop indicating output from the drop pulse extender, such that the no-drop detector will not be energized or change states every time a signal is received from the clock, which would in turn enable the latch to be triggered every other clock pulse.

The output from the latch and the reset output from the drop pulse extender are also connected with the no-drop alarm, such that under normal operating conditions the output of the drop pulse extender and of the latch will go negative at the same time, and the no-drop alarm will not be triggered, and the no-drop indicator will not be turned on. However, whenever a no-drop condition occurs, the output from the drop pulse extender will stay at a "one" state, enabling the no-drop alarm to be triggered on the next negative transition from the latch, and the no-drop indicator will thus be turned on indicating a fault condition. Further, the drop detector includes a pair of photodiodes or other sensing means disposed adjacent one another on one side of the drip chamber and accordingly the sensitivity of the unit is significantly increased, such that in the event of fogging or the like of the drip chamber wall, the sensor is still sensitive enough to detect the presence of a falling drop. Moreover, the use of two sensing means results in a broader field of view and thus a drop can be detected even though the set may not be supported in a true vertical position. Still further, if one sensor fails, the other can still sense the presence of a falling drop.

Accordingly, with the present invention an exceptionally accurate and reliable electronically controlled intravenous infusion set is provided which is both simple and economical, and the circuit is maintained in a locked or latched condition under normal circumstances, and is unlocked or unlatched for each drop. Moreover, in accordance with the present invention, a unique drip chamber has a valve in the outlet portion thereof for controlling flow through an IV set provided with the present invention.

OBJECTS OF THE INVENTION

It is an object of this invention to provide an electronically controlled IV set for accurately controlling the rate of flow of fluid being administered intravenously to a patient, and wherein an internal valve means and external drop sensing means are provided in the set operative to control flow through the set in response to a signal provided from a timer mechanism and operative to control flow without pinching, penetrating, or otherwise deforming the IV set.

Another object of this invention is to provide an electronically controlled IV set for intravenous administration of fluids to a patient wherein an electromagnetically operated valve is provided in the set and a control circuit is connected with the valve and includes both integrated circuits and discrete components, with all logic functions being accomplished via integrated circuits, and wherein the circuit is operative to maintain the valve de-energized or latched under normal conditions, and to unlock or energize the valve for obtaining each drop.

A further object of the invention is to provide a drip chamber for an IV set, wherein a valve for controlling flow through the drip chamber is provided in a lower portion of the drip chamber itself.

Yet another object of the invention is to provide an intravenous infusion set in which an electronically controlled valve is utilized to control the drip rate through the set, and wherein magnet means are provided for holding the valve open to enable flushing of the set or to enable flow even in the event of a power failure or if the patient is being transported from one location to another.

DETAILED DESCRIPTION OF THE INVENTION

Figure 1:
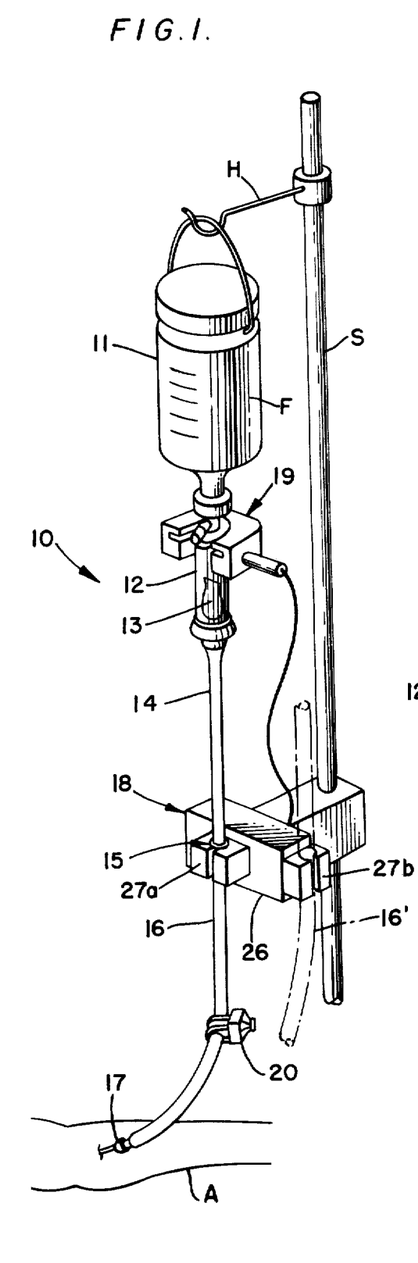
FIG. 1 is a perspective view of a first form of the invention, wherein the sensing device is mounted to the drip chamber of an IV set and the control valve and circuitry therefor are connected with the IV tubing between the ends thereof.

In the drawings, wherein like reference numerals indicate like parts throughout the several views, an IV set is indicated generally at 10 and includes a bottle or bag or other suitable supply 11 of IV fluid F, suitably suspended or supported from a hook H carried by an upright post or support S. A drip chamber 12 is connected to the bottom of the supply 11 in a conventional manner, and typically the drip chamber 12 has a piercing end 12a thereon which is inserted into the bottom end of the supply 11. A suitable filter means 13 is preferably provided in the drip chamber 12 for filtering contaminants from the fluid F. A length of IV tubing 14 is connected with the drip chamber at one end and is connected with an internal valve means 15 at its other end, and a second length of IV tubing 16 is connected at one of its ends with the valve means 15 and at its other end with a suitable needle or the like 17 for insertion into the arm or the like A of a patient for intravenous administration of fluids to the patient. The drip chamber and length of IV tubing define a fluid flow passage means for the IV fluid.

A suitable electronic control means 18 is operatively associated with the valve means 15 and is caused to energize the valve means in response to a preset signal. The control means 18 is also connected with a suitable photoelectric sensing means 19 positioned on the drip chamber 12 for sensing a drop of fluid F falling through the drip chamber and sending a signal to the control means to reset it. A manually operated clamp 20 of substantially conventional construction is provided on the IV tubing 16.

Figure 2:
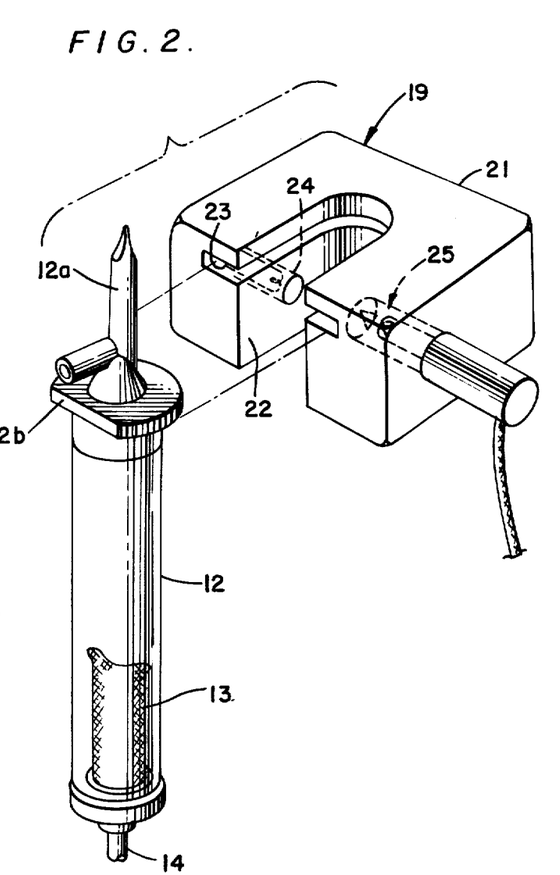
FIG. 2 is an enlarged, exploded view of the drip chamber and sensing device of the first form of the invention.
Figure 6:
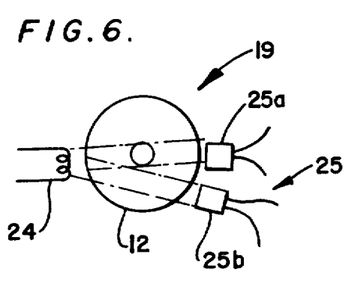
FIG. 6 is a diagrammatic plan view of a first form of photoelectric sensing means in accordance with the invention.

The photoelectric sensing device or drop detector 19 is preferably of molded plastic and comprises a generally U-shaped housing 21 having an elongate slot or notch 22 in one side thereof, with a generally U-shaped channel or groove 23 in the body extending around the notch 22 adjacent the upper portion thereof. A suitable light source 24 is in the housing 21 adjacent one side of the notch 22, and a suitable light sensitive means 25, such as a pair of photo-diodes 25a and 25b or the like, is in the housing 21 at the other side of notch 22 in alignment with the light source 24. The provision of a pair of photodiodes 25a and 25b, disposed side-by-side on the opposite side of the drip chamber 12 from the light source 24, as seen in FIG. 6, substantially eliminates the danger of an improper or erratic reading in the event the drip chamber wall becomes fogged or drops form on the wall thereof, since the two photodiodes significantly increase the sensitivity of the device, and even in the event of the photodiodes 25a or 25b becoming partially blocked by such fogging or drops forming on the wall of the drip chamber, the circuit remains balanced, whereby a drop falling through the drip chamber will interrupt the beam of light to the photodiode and cause a voltage change at the photodiode 25a to thus generate a signal to operate the device. Further, by using two photodiodes, even if the device is not accurately vertically suspended, the sweep of the sensor is such that a falling drop is still detected, even though it does not fall through the center of the device. In use, the drop detector 19 is mounted to the drip chamber 12 by inserting the drip chamber into the notch 22 with the flange 12b at the upper end of the drip chamber received in the groove 23 in the housing 21, and with the light source 24 and light sensitive means 25 disposed substantially at diametrically opposite sides of the drip chamber 12, so that a drop falling through the drip chamber will interrupt the beam of light from light source 24 and cause a voltage change at the photodiode 25, to thus transmit a signal to the control means 18.

Figure 3:
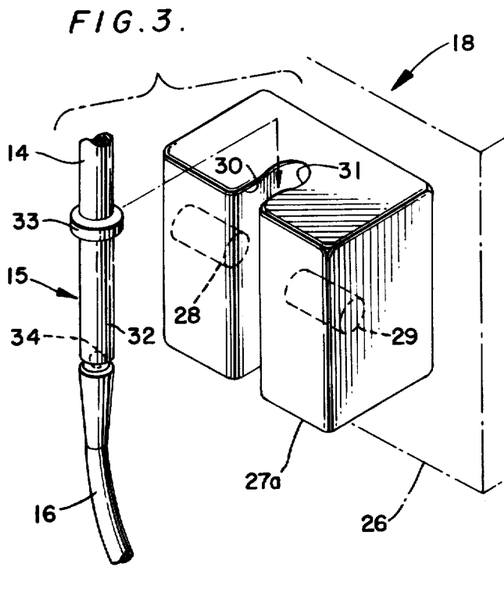
FIG. 3 is an enlarged, perspective view of the control valve and a portion of the IV tubing and of the electromagnet means for operating the valve.

The control means 18 includes a suitable housing or control box 26 in which the circuitry is contained, and an electrically controlled valve operating housing 27a in which a pair of electromagnets 28 and 29 are disposed on opposite sides of a slot or notch 30, which is slightly enlarged at its rear side or edge 31 and is constructed in relation to the size of the valve means 15, such that the valve means may be inserted through the slot 30 and pulled downwardly into the enlarged portion 31.

Figure 4:
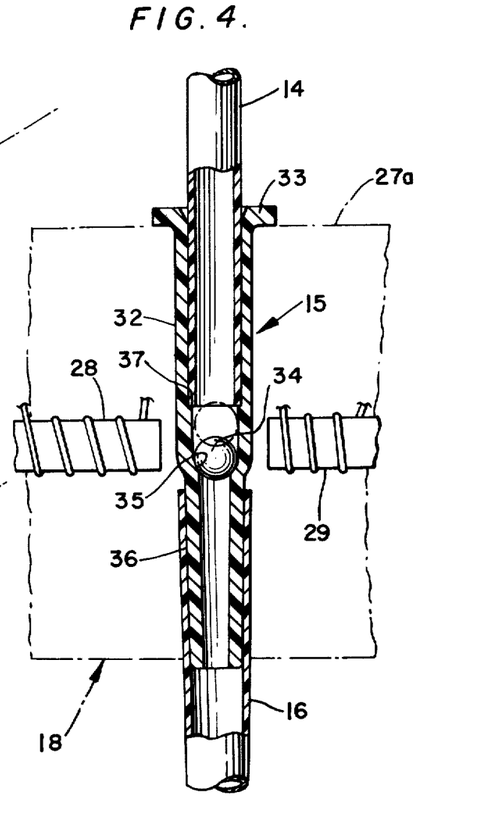
FIG. 4 is a greatly enlarged, fragmentary view in section of the valve and its relationship with the electromagnet means.

The valve means preferably comprises a one-piece, elongate, plastic, tubular valve housing 32, having a radially outwardly directed flange 33 on the upper end thereof, which is aranged to seat against the upper surface of the housing 27a to accurately locate the housing and valve ball 34 contained therewithin relative to the electromagnets 28 and 29. The housing 32 is tapered inwardly between its ends to define an upwardly facing valve seat 35 against which the valve ball 34 seats under the action of gravity and the pressure of fluid above the valve, and the lower end 36 of the housing is gradually inwardly tapered for reception thereover of the end of IV tubing 16. The inlet section 14 of IV tubing to the valve 15 is secured within the upper portion of the valve housing 32, and the lower end of the IV tubing 14 is abutted against a narrow, annular, upwardly facing shoulder 37 in the bore of the upper portion of housing 32 to correctly space the end of the IV tubing 14 from the ball valve 34.

Figures 9, 11:
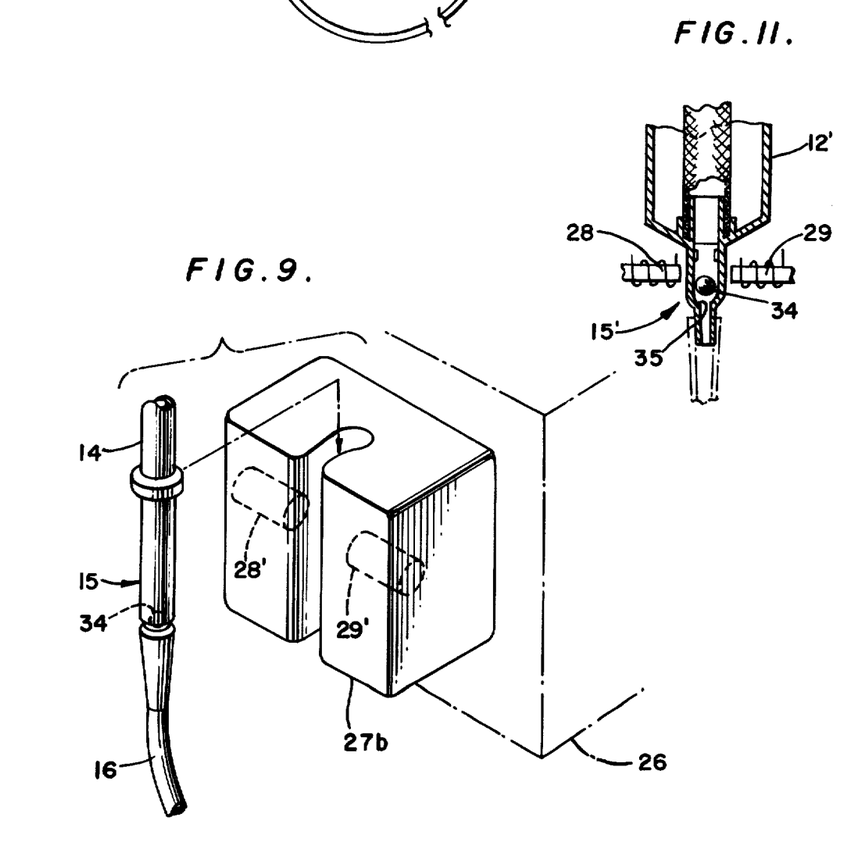
FIG. 9 is a view similar to FIG. 3, of the permanent magnet means for holding the valve open.
FIG. 11 is a fragmentary, enlarged view in section of the drip chamber of FIG. 10, showing the position of the valve in relation to the drip chamber.

As seen in FIGS. 1 and 9, a permanent magnet or housing means 27b is also provided on the control unit 18, and is substantially similar to the electromagnet means 27a in FIG. 3, except that rather than electromagnets 28 and 29, permanent magnets 28' and 29' are provided. Thus, if it is desired to flush the set, the valve means 15 is merely placed in position in housing 27b and the permanent magnet means holds the valve open, and with clamp 20 opened, full flow is achieved through the set to flush it. Moreover, in the event of a power failure or the like, the valve means 15 may be positioned in the permanent magnet housing and the clamp 20 adjusted to obtain the desired flow rate. Still further, if it is necessary or desirable to transfer the patient from one location to another, the permanent magnet and clamp can be used to control flow while the patient is in transit.

Figure 5:
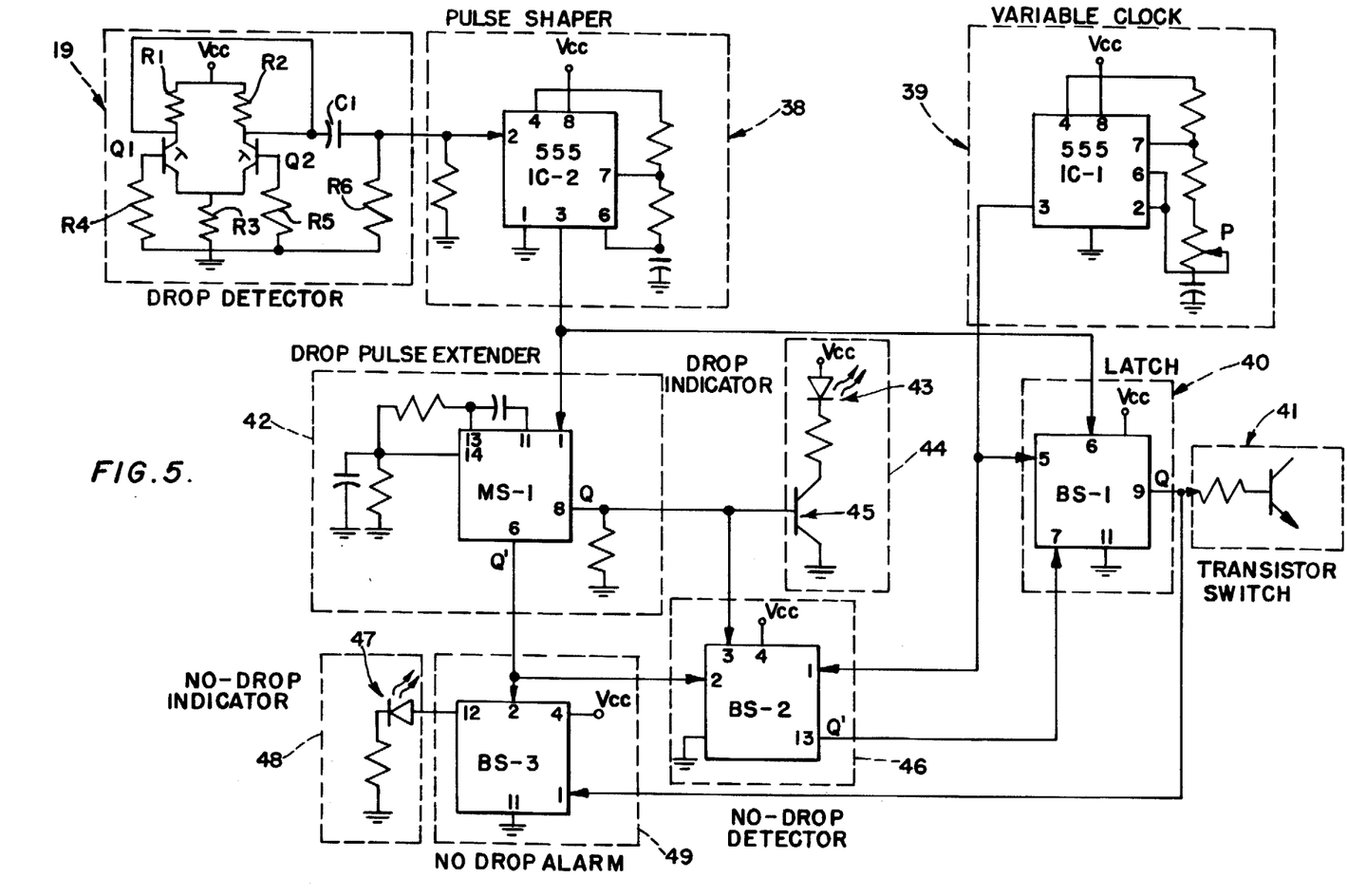
FIG. 5 is a schematic view of the circuit for the electronic control of the invention.

The control circuit for controlling operation of the ball valve 34 and thus for controlling the drop rate, and accordingly the rate of flow of fluid through the set, includes variable timer means 39 having means to generate a plurality of pulses per unit of time directly corresponding to a desired number of drops of IV fluid per unit of time, first switch means 40, 41 connected in the circuit means between the timer means and the valve operating means and operative to maintain the valve operating means deenergized until a pulse is received from the timer means and than operative to energize the valve operating means to open the valve and hold it open until a drop falls, drop detector means 19 operatively associated with the drip chamber to sense a drop falling through the drip chamber and generate a pulse in response thereto, said drop detector means operatively connected with the first switch means to send the pulse generated upon sensing a drop to the first switch means to reset the switch means and thus de-energize the valve operating means when a drop is sensed by the drop detector means, and no-drop detector means including a second switch means 46 operatively connected in the circuit means with the first switch means to send a signal to the first switch means to inhibit the first switch means and prevent energization of the valve operating means in the absence of drop pulses between the successive clock pulses.

As seen in FIG. 5, the drop-detector 19 includes a pair of NPN photo transistors Q1 and Q2 arranged as a comparative circuit, and light striking the emitter-base junctions of the transistors causes current to flow through the emitter bias resistor R3, the transistors Q1 and Q2 and the load resistors R1 and R2 to the supply voltage $V_{cc}$. In this conducting state, the collector voltage is low, at some point near ground. When the light source is interrupted by a drop, current flow drops through the circuit and the collector voltage rises to a level near the supply voltage. This action appears as a pulse at the input of the differentiating network, including capacitor C1 and resistor R6. In the event the drip chamber becomes fogged or if droplets form on the surface of the drip chamber wall and such fogging or droplets reduce the amount of light striking the phototransistors Q1 and Q2, the circuit will remain balanced. A drop falling past the phototransistor will thus cause a pulse to appear at the input of the differentiating network and thus at the input to pin 2 of the 555 integrated circuit chip IC-2 of the pulse shaper 38.

A timer or clock 39 also includes a 555 integrated circuit chip IC-1, having its output pin 3 connected with clock input pin 5 of J-K bistable flip-flop BS-1 of latch 40. The frequency at which the output of IC-1 changes states can be varied by changing the setting of potentiometer P connected with pins 2, 6 and 7 of IC-1, and thus the drip rate of the IV set can be varied in accordance with the change in frequency of the signal from pin 3 of the clock 39. The output of IC-1 alternates between a logic "one" and a logic "zero" and the negative transition of going from a one to a zero determines when a drop starts to form, since the negative signal of the clock is conducted to the input pin 5 of the J-K bistable flip-flop BS-1 of the latch 40, and this causes the flip-flop BS-1 to change states. In other words, the Q output of BS-1 is normally a zero out and is fed into the base of a transistor switch 41, which is connected between a source of power and the electromagnet means 28 and 29 is normally in a nonconducting state, such that the electromagnets are normally de-energized. A zero on the base of the transistor keeps it turned off. However, when BS-1 changes states, as, for example, when the negative pulse is received at pin 5 from pin 3 of the clock, the Q output of BS-1 goes to a one and the transistor switch 41 is now biased forward, enabling current to flow from the power supply to the electromagnets 28 and 29, thus opening the valve and enabling a drop to form in the drip chamber 12. When the drop falls, it interrupts the light path to the photodiodes 25a and 25b in the drop detector circuit, and this interruption causes a sudden change in the photodiodes' resistance, resulting in a voltage change that is capacitively coupled to the input pin 2 of IC-2. Every time a drop falls, a negative pulse is produced at the output pin 3 of IC-2, and this negative pulse is sent to a reset pin 6 of BS-1 in the latch 40 to reset the bistable flip-flop BS-1. The Q output of BS-1 now goes back to a zero, turning off the transistor switch, which stops the current flow to the electromagnet, enabling the magnetically responsive ball or other type valve 34 to seat on its seat 35 under the influence of gravity and fluid pressure above the ball. Thus, only one drop at a time can fall, at a predetermined rate established by the setting of the potentiometer P of the clock 39. In other words, the fluid path of the IV set is opened on the negative transition of the IC-1 output and is closed on the negative transition of the IC-2 output, i.e., when a drop falls from the drip device in the IV chamber. The output of IC-2 in the pulse shaper is also used to trigger a monostable multivibrator MS-1 in a drop pulse extender 42. This extension of the pulse from the pulse shaper 38 is necessary, since the Q output of the monostable multivibrator MS-1 is used to turn on a light emitting diode 43 in the drop indicator 44 via an NPN driver transistor 45. If the output of IC-2 was used directly, the light emitting diode 43 would not be turned on long enough to be detected visually.

A second J-K bistable flip-flop BS-2 is employed to detect a no-drop condition, and its clock input pin 1 is connected to the output pin 3 of IC-1. A connection is also made between pin 6 of monostable multivibrator MS-1 and reset pin 2 of the bistable flip-flop BS-2 to reset the flip-flop BS-2 when a pulse is fed from the output Q' of the multivibrator MS-1. The negative transitions of the output Q' from pin 6 of monostable multivibrator MS-1 occur almost exactly in time with those of IC-2, and accordingly, under normal operating conditions the changing of states of the bistable flip-flop BS-1 and the bistable flip-flop BS-2 will be coincident.

Pin 13 of bistable flip-flop BS-2 in the no-drop detector 46 is connected with pin 7 of the J input of the bistable flip-flop BS-1 of the latch 40, and in normal operation will be high, causing the latch 40 to switch the Q output thereof from a low to a high in response to each clock pulse. However, when a no-drop condition occurs, as for example, when the IV bottle is empty or the tubing is pinched and the like, the flip-flop BS-2 will not be reset after being triggered by a pulse from IC-1, thus the Q' output of BS-2 will now stay at a logic zero, and this zero, applied to the input pin 7 of BS-1, will cause the flip-flop BS-1 to respond to subsequent clock pulses by driving the Q output to a zero and keeping such Q output at a zero as long as no drops are detected.

Further, the bistable flip-flop BS-2 is locked up by feeding a signal to pin 3 thereof from the Q output or pin 8 of monostable multivibrator MS-1. If this were not done, the bistable flip-flop BS-2 would change states with very negative transition from the chip IC-1 of clock 39 and bistable flip-flop BS-1 of latch 40 would, therefore, be triggered every other clock pulse.

A no-drop condition is visually indicated by turning on a light emitting diode 47 in a no-drop indicator 48 via a third bistable flip-flop BS-3 in a no-drop alarm 49. The clock input pin 1 of BS-3 is connected with the Q output or pin 9 of BS-1 and the reset input of BS-3 at pin 2 is fed by the Q' output of monostable multivibrator MS-1. Under normal operating conditions, the Q' output of MS-1 and the Q output of BS-1 will go negative at the same time, and when this happens, BS-3 will not trigger and the no-drop light emitting diode 47 will not be turned on. However, whenever a no-drop condition occurs, the Q' output of multivibrator MS-1 will stay at a one state, enabling flip-flop BS-3 to be triggered on the next negative transition from flip-flop BS-1. When the flip-flop BS-1 is triggered, the no-drop light emitting diode is turned on, indicating a fault condition. After the Q output of flip-flop BS-1 goes negative, triggering the flip-flop BS-3, it will remain locked in that state because of the inhibiting action of the flip-flop BS-2 in the no-drop detector 46. The unit, under these conditions, will remain locked up until the fault condition is corrected.

Figure 7:
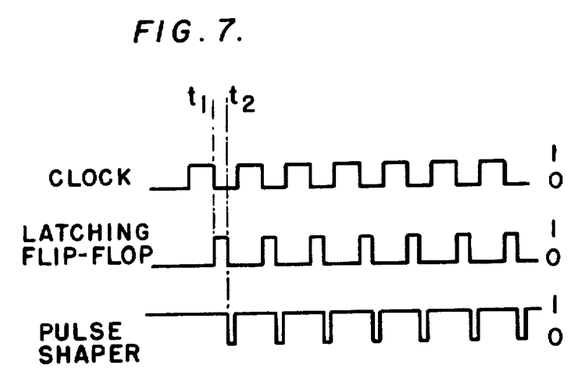
FIG. 7 is a chart illustrating the signal relationship of the clock, latch and pulse shaper of the invention.

In the chart of FIG. 7, the line $t_1$ indicates the negative transition of a clock pulse, and at this point the latching flip-flop BS-1 goes to logic one and the transistor switch 41 is turned on, enabling the electromagnets to be energized and a drop, therefore, starts to fall. At time $t_2$ the drop falls and is detected by the photodiodes and a reset pulse from the pulse shaper resets the latching flip-flop BS-1 and the electromagnets are de-energized. As can be seen, the signals produced and thus the drip rate of the set are precise and can be predetermined and controlled with great accuracy and reliability.

Figure 10:
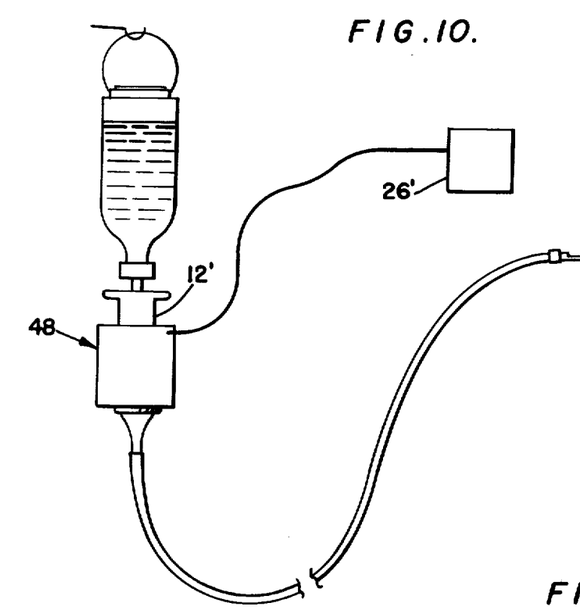
FIG. 10 is a schematic, perspective view of a second form of electronically controlled IV set in accordance with the invention, wherein the sensing device, control valve and circuitry therefor are all positioned on the drip chamber.

In FIGS. 10 and 11, a modified form of the invention is illustrated, and in this form of the invention, the operation of the components is exactly as described above and the circuitry is as described above. However, in this form of the invention, rather than providing the ball valve means 15 in the length of IV tubing, the ball valve 15' is provided in the lower end of a modified drip chamber 12', and the electromagnets 28 and 29 are positioned adjacent the extension on a lower end of the drip chamber 12' to attract the ball 34 upwardly away from the seat 35 to enable a drop to form in the drip chamber 12', as described previously. Thus, the sensing means and electromagnets are housed in a member 48, which is preferably suitably supported, and the drip chamber 12' is also operatively positioned relative to the member 48, so that the drop sensing means is positioned to sense a drop falling through the drip chamber and so that the electromagnets are positioned to raise the ball from its seat.

Figure 8:
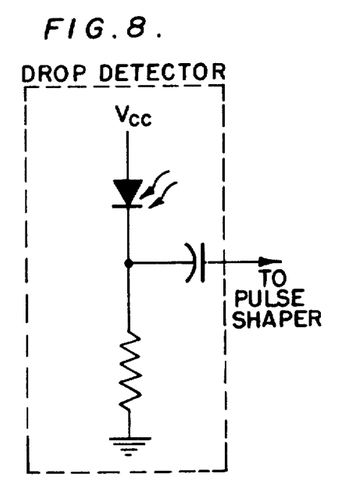
FIG. 8 is a schematic circuit diagram of a second form of drop detector in accordance with the invention.

In FIG. 8, a modified sensing means 19' includes only a single photodiode 25 to sense a falling drop. In all other respects, the apparatus and operation are as described previously.

In summation, a switch means is connected between the timer means and the valve operating means and is operative to maintain the valve operating means deenergized until a pulse is received from the timer means and then is operative to energize the valve operating means to open the valve and hold it open until a drop falls. A drop detector means is operatively associated with the drip chamber to sense a drop falling through the drip chamber and to generate a pulse in response thereto, and the drop detector means is operatively connected with the switch means to send the pulse generated upon sending a drop to the switch means to reset the switch means and thus de-energize the valve operating means when a drop is sensed by the drop detector means. A no-drop detector means, including a switch means, is operatively connected with the drop detector means to receive a pulse therefrom as each drop is sensed, and is connected with the timer means to receive each pulse therefrom, and is operatively connected with the switch means to send a signal to the switch means to lock or inhibit the switch means and prevent energization of the valve operating means when a pulse is received from the timer means, but no pulse is received from the drop detector means.

It is clear, therefore, that the no-drop detector is operative to indicate a no-drop condition when a pulse is received from the timer means, but no pulse is received from the drop detector means, and operative to lock the latching flip-flop and prevent energization of the valve operating means when said no-drop condition is sensed. In other words, the no-drop detector means is operative when no drop falls, and two pulses are thus sequentially generated by the timer means in the absence of an intervening pulse from the drop detector means, to send a signal to the switch means to inhibit the switch means and prevent energization of the electromagnet means. As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

We claim:

1. An electronically controlled intravenous infusion set, comprising: a supply of intravenous fluid; a drip chamber connected with said supply; a length of IV tubing connected with the drip chamber for receiving IV fluid from the supply and drip chamber; said drip chamber and length of IV tubing comprising a fluid flow passage means; valve means connected in the intravenous infusion set downstream of the supply of IV fluid within the flow passage means and being operated between open and closed positions; valve operating means external of the flow passage means and operative to operate the valve means between open and closed positions to control flow of IV fluid through the intravenous infusion set; electrical circuit means connected with the valve operating means to control operation of the valve means, said circuit means including a variable timer means having means to generate a plurality of pulses per unit of time at a constant repetition rate and directly corresponding to a desired number of drops of IV fluid per unit of time, a bistable latching flip-flop connected between the timer means and the valve operating means and operative to maintain the valve operating means de-energized until a pulse is received from the timer means and then operative to enable energization of the valve operating means to open the valve and hold the valve open until a drop falls, drop detector means operatively associated with the drip chamber to sense a drop falling through the drip chamber and produce a pulse in response thereto, said drop detector means operatively connected with the bistable latching flip-flop to send the pulse thereto produced when a drop is sensed to reset the flip-flop and thus de-energize the valve operating means to enable the valve to close, and no-drop detector means operatively connected with the drop detector means and with the timer means and bistable latching flip-flop and operative to receive a pulse from the drop detector means when a drop is sensed and to receive pulses from the timer means to indicate a no-drop condition when a pulse is received from the timer means but no pulse is received from the drop detector means, and including means operative to send a signal to the latching flip-flop in response to sensing said no-drop condition to lock the latching flip-flop and prevent energization of the valve operating means when said no-drop condition is sensed.

2. An electronically controlled intravenous infusion set as in claim 1, wherein a pulse shaper means is operatively connected with the drop detector means to amplify and square the pulse generated by the drop detector means, a drop pulse extender operatively connected with the pulse shaper to extend the width of said shaped pulse, and a drop indicator operatively connected with the drop pulse extender to receive the extended pulse therefrom and to visually indicate a drop falling through the drip chamber.

3. An electronically controlled intravenous infusion set as in claim 2, wherein the pulse shaper and timer both include integrated circuit chips, the latching flip-flop and the no-drop detector means both include J-K bistable flip-flops, and the drop pulse extender means includes a monostable multivibrator.

4. An electronically controlled intravenous infusion set as in claim 3, wherein a no-drop alarm means is operatively connected with the latching flip-flop and with the drop pulse extender to indicate when a no-drop condition occurs, said no-drop detector means operatively connected with the drop pulse extender to lock the no-drop detector means and said no-drop detector means operatively connected with the latching flip-flop to lock the latching flip-flop when the no-drop detector means is locked, to thus prevent operation of the valve means under no-drop conditions.

5. An electronically controlled intravenous infusion set as in claim 1, wherein said drop sensing means comprises a molded plastic housing of generally U-shaped configuration and has an elongate notch in one side thereof for receiving the drip chamber, and means in said housing for securing the drip chamber in a predetermined operative position, said drop sensing means having a light source and a light sensitive means therein on opposite sides of the notch therein and disposed to be positioned at substantially diametrically opposite sides of the drip chamber to sense a drop falling through the drip chamber.

6. An electronically controlled intravenous infusion set as in claim 5, wherein the valve operating means and circuit means are contained in a housing means, said housing means having means thereon for attachment thereto of the valve means and IV tubing, so that the valve means is maintained in a predetermined operative position relative to the valve operating means.

7. An electronically controlled intravenous infusion set as in claim 6, wherein the valve means comprises an elongate tubular valve body mounted between the ends of the length of IV tubing, said valve body having an inwardly tapered portion defining an axially facing valve seat, a magnetically responsive ball in the body cooperative with the valve seat and movable under the action of gravity to a closed position, said valve operating means comprising electromagnets positioned relative to the ball to raise the ball from its seat when the electromagnets are energized.

8. An electronically controlled inravenous infusion set as in claim 6, wherein the drop sensing means and the valve operating means are disposed in a housing having means for operatively positioning the drip chamber in the housing, said drip chamber having an extension on one end thereof, an axially facing valve seat in said extension, a valve in said extension cooperable with said valve seat between open and closed positions, and said valve operating means comprising electromagnets positioned relative to said ball to operate said ball to its open position away from said seat.

9. An electronically controlled intravenous infusion set as in claim 1, including a housing, said valve operating means mounted on said housing, said housing having means for attachment thereto of said length of IV tubing, said valve means being in the length of IV tubing and positionable in said housing in operative relationship with said valve operating means, and a permanent magnet means carried by the housing and having means for operative association therewith of said valve means to maintain the valve means in open position to enable flushing of the intravenous infusion set and to enable flow of IV fluid in the event of a power failure or the like.

10. A drip chamber as in claim 1, wherein a permanent magnet means is operatively positionable relative to said valve to maintain the valve in open position to enable flushing of the intravenous infusion set and to enable flow of IV fluid in the event of a power failure or the like.

11. A drip chamber as in claim 10, wherein said valve is a ball valve.

12. An intravenous infusion set as in claim 1, wherein the valve means comprises an extended portion of the drip chamber, an axially upwardly facing valve seat in the extended portion, a magnetically attractive valve in the extended portion cooperable with the valve seat and maintained in closed position under the action of gravity, and said valve operating means comprising electromagnet means externally of the drip chamber adjacent the valve to operate the valve to its open position upon energization of the electromagnet means.

13. An electronically controlled intravenous infusion set for use with a supply of intravenous fluid, comprising: a drip chamber connected with said supply; a length of IV tubing connected with the drip chamber for receiving IV fluid from the drip chamber; said drip chamber and length of IV tubing comprising a fluid flow passage means; valve means connected in the intravenous infusion set downstream of the supply of IV fluid within the flow passage means and operable between open and closed positions; valve operating means external of the flow passage means and operative to operate the valve means between open and closed positions to control flow of IV fluid through the intravenous infusion set; electrical circuit means connected with the valve operating means to control operation of the valve means, said circuit means including variable timer means having means to generate a plurality of pulses per unit of time directly corresponding to a desired number of drops of IV fluid per unit of time, first switch means connected in the circuit means between the timer means and the valve operating means and operative to maintain the valve operating means de-energized until a pulse is received from the timer means and then operative to energize the valve operating means to open the valve and hold it open until a drop falls, said first switch means capable of being inhibited upon receipt of a predetermined signal, drop detector means operatively associated with the drip chamber to sense a drop falling through the drip chamber and generate a pulse in response thereto, said drop detector means operatively connected with the first switch means to send the pulse generated upon sensing a drop to the first switch means to reset the first switch means and thus de-energize the valve operating means when a drop is sensed by the drop detector means, and no-drop detector means including a second switch means operatively connected in the circuit means with the first switch means and with the drop detector means and timer means to receive pulses from the drop detector means and timer means to detect the absence of drop pulses between successive clock pulses, and said second switch means operative to send a signal to the first switch means to inhibit the first switch means and prevent energization of the valve operating means in the absence of drop pulses between successive clock pulses.

14. An intravenous infusion set as in claim 13, wherein the valve means comprises an extended portion of the drip chamber, an axially upwardly facing valve seat in the extended portion, a magnetically attractive valve in the extended portion cooperable with the valve seat and maintained in closed position under the action of gravity, and said valve operating means comprising electromagnet means externally of the drip chamber adjacent the valve to operate the valve to its open position upon energization of the electromagnet means.

* * * * *